US009111020B2

(12) United States Patent
Plavnik et al.

(10) Patent No.: US 9,111,020 B2
(45) Date of Patent: Aug. 18, 2015

(54) ARCHITECTURE AND METHODS FOR SOPHISTICATED DISTRIBUTED INFORMATION SYSTEMS

(75) Inventors: Michael Plavnik, Mahwah, NJ (US);
Vitaly Roginsky, Ramsey, NJ (US);
Alex Jurovitsky, Mahwah, NJ (US);
Alexander Natanzon, Mahwah, NJ (US); Dmitry Pavlov, New Paltz, NY (US)

(73) Assignee: General Electric Company, Schenectady, NY (US)

( * ) Notice: Subject to any disclaimer, the term of this patent is extended or adjusted under 35 U.S.C. 154(b) by 1876 days.

(21) Appl. No.: 12/054,165

(22) Filed: Mar. 24, 2008

(65) Prior Publication Data

US 2008/0262875 A1 Oct. 23, 2008

Related U.S. Application Data

(60) Provisional application No. 60/919,655, filed on Mar. 24, 2007.

(51) Int. Cl.
| | |
|---|---|
| *G06Q 50/00* | (2012.01) |
| *G06Q 10/00* | (2012.01) |
| *G06Q 50/24* | (2012.01) |
| *G06F 19/00* | (2011.01) |
| *G06Q 50/22* | (2012.01) |

(52) U.S. Cl.
CPC ............ *G06F 19/327* (2013.01); *G06F 19/321* (2013.01); *G06Q 50/22* (2013.01); *G06Q 50/24* (2013.01)

(58) Field of Classification Search
USPC .......................................................... 705/2–3
See application file for complete search history.

(56) References Cited

U.S. PATENT DOCUMENTS

| | | | |
|---|---|---|---|
| 2004/0030992 A1* | 2/2004 | Moisa et al. .................. 715/513 |
| 2004/0148382 A1* | 7/2004 | Narad et al. .................. 709/223 |
| 2005/0080801 A1* | 4/2005 | Kothandaraman et al. ... 707/100 |
| 2007/0136089 A1* | 6/2007 | Schneider et al. ................ 705/2 |

* cited by examiner

*Primary Examiner* — Minnah Seoh
(74) *Attorney, Agent, or Firm* — Hanley, Flight and Zimmerman, LLC

(57) ABSTRACT

Certain embodiments of the present invention provide systems and methods for distributed information systems and architectures. Certain embodiments provide a distributed healthcare information system. The distributed information system includes a back-end subsystem providing content including services, applications, and workflows for healthcare execution. The content is configured for generally application to a plurality of domains. The system also includes a platform subsystem providing domain specific extensions to customize the content of the back-end subsystem for particular domains. The platform subsystem is in communication with the back-end subsystem to access the content. The system further includes a front-end subsystem providing a graphical user interface for a user to access functionality and information based on the content as customized by the domain specific extensions. The front-end subsystem is in communication with the platform subsystem to access the content.

20 Claims, 12 Drawing Sheets

ARCHITECTURE AND METHODS FOR SOPHISTICATED DISTRIBUTED INFORMATION SYSTEMS

RELATED APPLICATIONS

The present application claims the benefit of priority to U.S. Provisional Application No. 60/919,655, filed on Mar. 24, 2007, entitled "Novel Architecture and Methods for Sophisticated Distributed Information Systems", which is herein incorporated by reference in its entirety.

FEDERALLY SPONSORED RESEARCH OR DEVELOPMENT

Not Applicable

MICROFICHE/COPYRIGHT REFERENCE

Not Applicable

BACKGROUND OF THE INVENTION

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during and/or after surgery, medical personnel may access patient information, such as images of a patient's anatomy, that are stored in a medical information system. Radiologist and/or other clinicians may review stored images and/or other information, for example.

Using a PACS and/or other workstation, a clinician, such as a radiologist, may perform a variety of activities, such as an image reading, to facilitate a clinical workflow. A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper. The practitioner, such as a radiologist or cardiologist, typically uses other tools to perform diagnosis. Some examples of other tools are prior and related prior (historical) exams and their results, laboratory exams (such as blood work), allergies, pathology results, medication, alerts, document images, and other tools. For example, a radiologist or cardiologist typically looks into other systems such as laboratory information, electronic medical records, and healthcare information when reading examination results.

PACS were initially used as an information infrastructure supporting storage, distribution, and diagnostic reading of images acquired in the course of medical examinations. As PACS developed and became capable of accommodating vast volumes of information and its secure access, PACS began to expand into the information-oriented business and professional areas of diagnostic and general healthcare enterprises. For various reasons, including but not limited to a natural tendency of having one information technology (IT) department, one server room, and one data archive/backup for all departments in healthcare enterprise, as well as one desktop workstation used for all business day activities of any healthcare professional, PACS is considered as a platform for growing into a general IT solution for the majority of IT oriented services of healthcare enterprises.

However, creation of a unified information system across a multi-specialty and multi-site distributed enterprise presents several challenges to a technology and service vendor. For example, software deployment, releases, and upgrades present challenges across multiple sites and multiple specialties. Storage expansion and maintenance, perceptive intelligence, and user-observable performance must also be addresses in a unified information system design and implementation. Scalability of storage, cost of ownership, number of applications, and/or throughput, for example, is a concern, as well as maintaining business continuity across an enterprise. With an information system, data redundancy, including fault tolerance and/or data recovery, is important. Further, having a cost- and business-effective service center providing autonomous workflows of independent federation objects, merge and split of federations, cross-organization policy, and/or security would be highly desirable.

BRIEF SUMMARY OF THE INVENTION

Certain embodiments of the present invention provide systems and methods for distributed information systems and architectures.

Certain embodiments provide a distributed healthcare information system. The distributed information system includes a back-end subsystem providing content including services, applications, and workflows for healthcare execution. The content is configured for generally application to a plurality of domains. The system also includes a platform subsystem providing domain specific extensions to customize the content of the back-end subsystem for particular domains. The platform subsystem is in communication with the back-end subsystem to access the content. The system further includes a front-end subsystem providing a graphical user interface for a user to access functionality and information based on the content as customized by the domain specific extensions. The front-end subsystem is in communication with the platform subsystem to access the content.

Certain embodiments provide a method for distribution of healthcare information and functionality. The method includes retrieving generalized content based on a request from a user interface front-end. The content includes services, applications, and workflows for healthcare execution. The content is configured to be generally applicable to a plurality of domains. The method also includes associating one or more domain specific extensions with the generalized content to customize the content for a particular domain. The method further includes providing the content with the one or more domain specific extensions to a user via the user interface front-end.

Certain embodiments provide a distributed information system utilizing domain model components, service components, and server components to provide information and functionality to a user. The distributed information system includes a back-end subsystem providing content including services, applications, and workflows. The content is configured for generally application to a plurality of domains and divided into a plurality of layers composable in various combinations. The system also includes a platform subsystem providing domain specific extensions to customize the content of the back-end subsystem for particular domains. The platform subsystem is in communication with the back-end subsystem to access the content. The system further includes a front-end subsystem providing a graphical user interface for a user to access functionality and information based on the content as customized by the domain specific extensions. The front-end subsystem is in communication with the platform subsystem to access the content.

Figure 1:
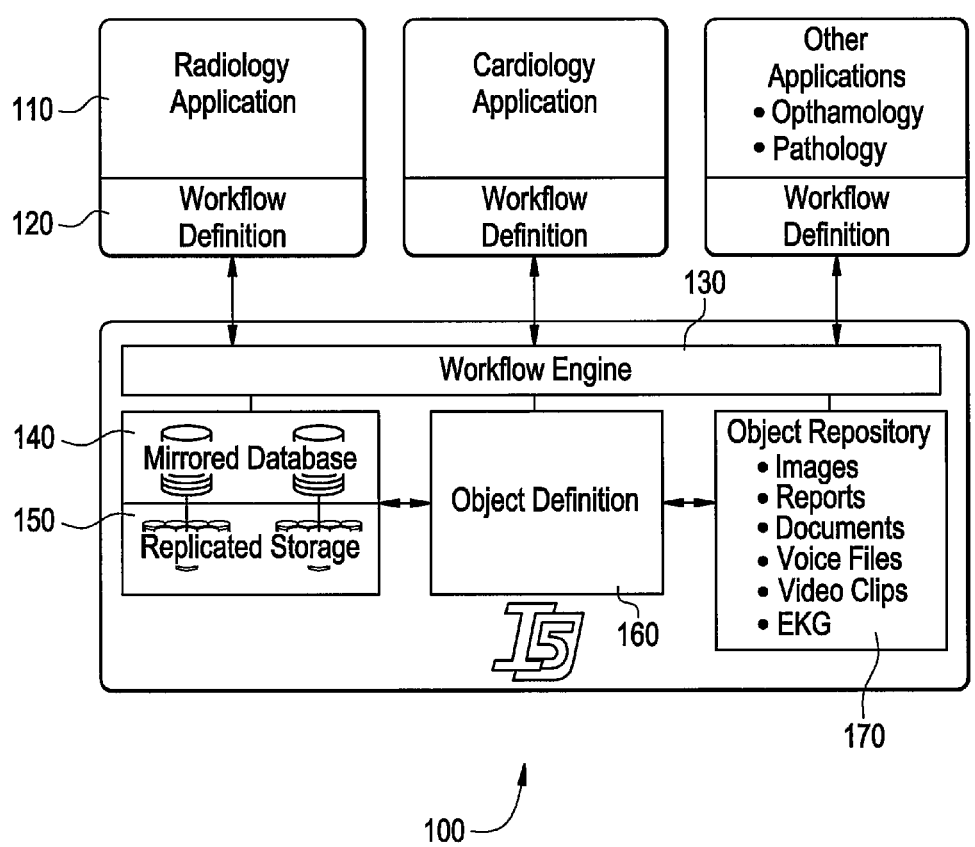
FIG. 1 demonstrates a business and application diagram for PACS information system in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Certain embodiments of the present invention provide a variety of methods and technologies for more effective development, deployment and support of sophisticated distributed information systems more uniformly encompassing various subspecialties and professional workflows. Certain embodiments help deliver cost effective, reliable, and secure products with a low cost of ownership, high reliability, and versatility. While healthcare enterprises represent a preferred environment for certain embodiments, it should be clearly understood that healthcare enterprises cannot be considered as the only area of application. For example, certain embodiments should be considered applicable to any field of development involving vending and support of distributed high-sophisticated information with strict requirements for reliability, secure data storage/data access and including multiplicity of the workflows for multiplicity of user groups of different subspecialties.

Certain embodiments provide an information system for a healthcare enterprise including a PACS IT system for radiology and/or other subspecialty system as demonstrated by the business and application diagram in FIG. 1. The system 100 of FIG. 1 includes a clinical application 110, such as a radiology, cardiology, ophthalmology, pathology, and/or application. The system 100 also includes a workflow definition 120 for each application 110. The workflow definitions 120 communicate with a workflow engine 130. The workflow engine 130 is in communication with a mirrored database 140, object definitions 60, and an object repository 170. The mirrored database 140 is in communication with a replicated storage 150. The object repository 170 includes data such as images, reports, documents, voice files, video clips, EKG information, etc.

Figure 2:
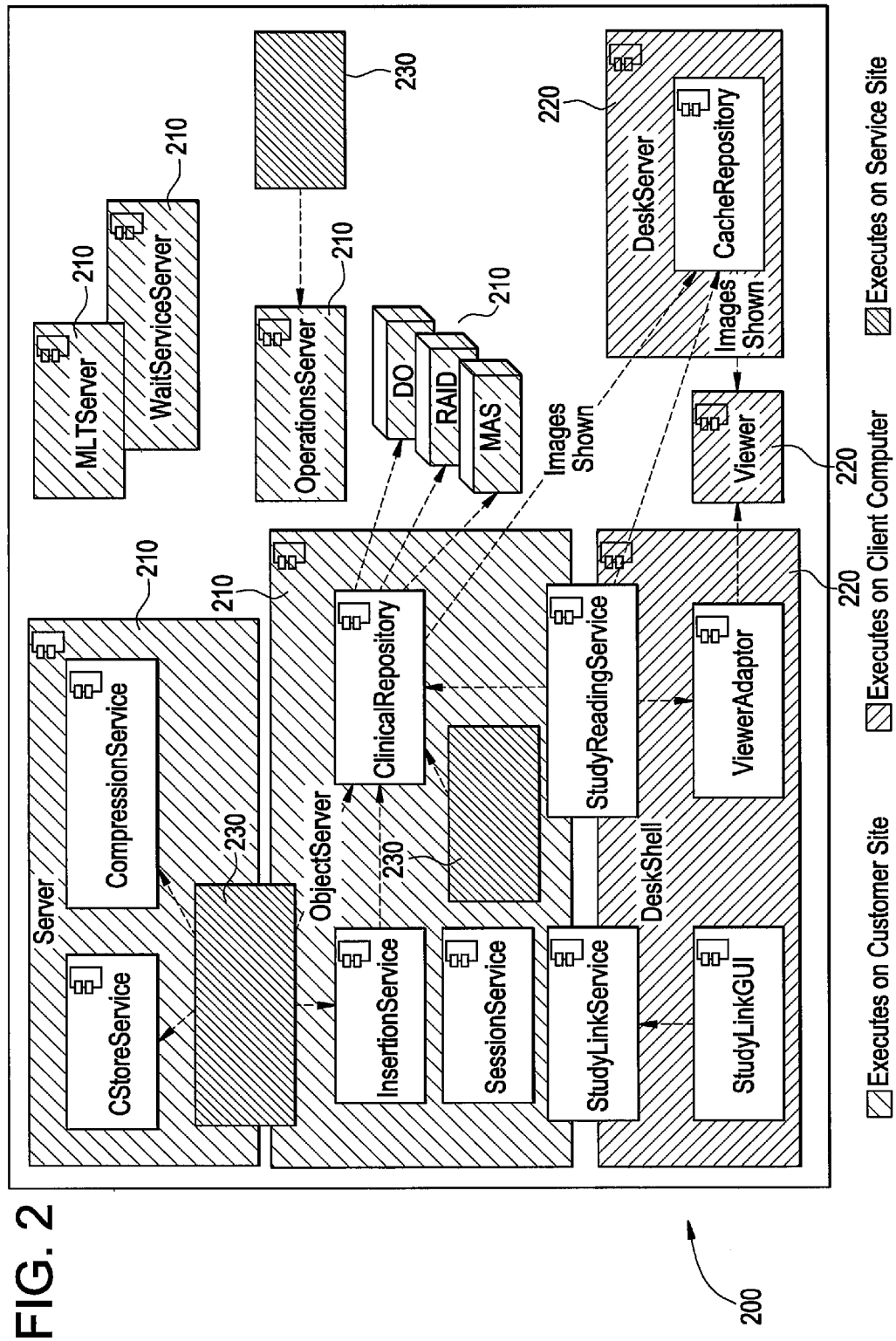
FIG. 2 illustrates an embodiment of an information system delivering application and business content in accordance with an embodiment of the present invention.

An embodiment of an information system that delivers application and business goals is presented in FIG. 2. The specific arrangement and contents of the assemblies constituting this embodiment bears sufficient novelty and constitute part of certain embodiments of the present invention. The information system 200 of FIG. 2 demonstrates services divided among a service site 230, a customer site 210, and a client computer 220. For example, a DicomServer, HL7Server, WebServicesServer, Operations Server, database and other storage, an ObjectServer, and ClinicalRepository execute on a customer site 210. A DeskShell, Viewer, and DeskServer execute on a client computer 220. A Dicom Controller, Compiler, and the like execute on a service site 230. Thus, operational and data workflow may be divided, and only a small display workload is placed on the client computer 220, for example.

Figure 3:
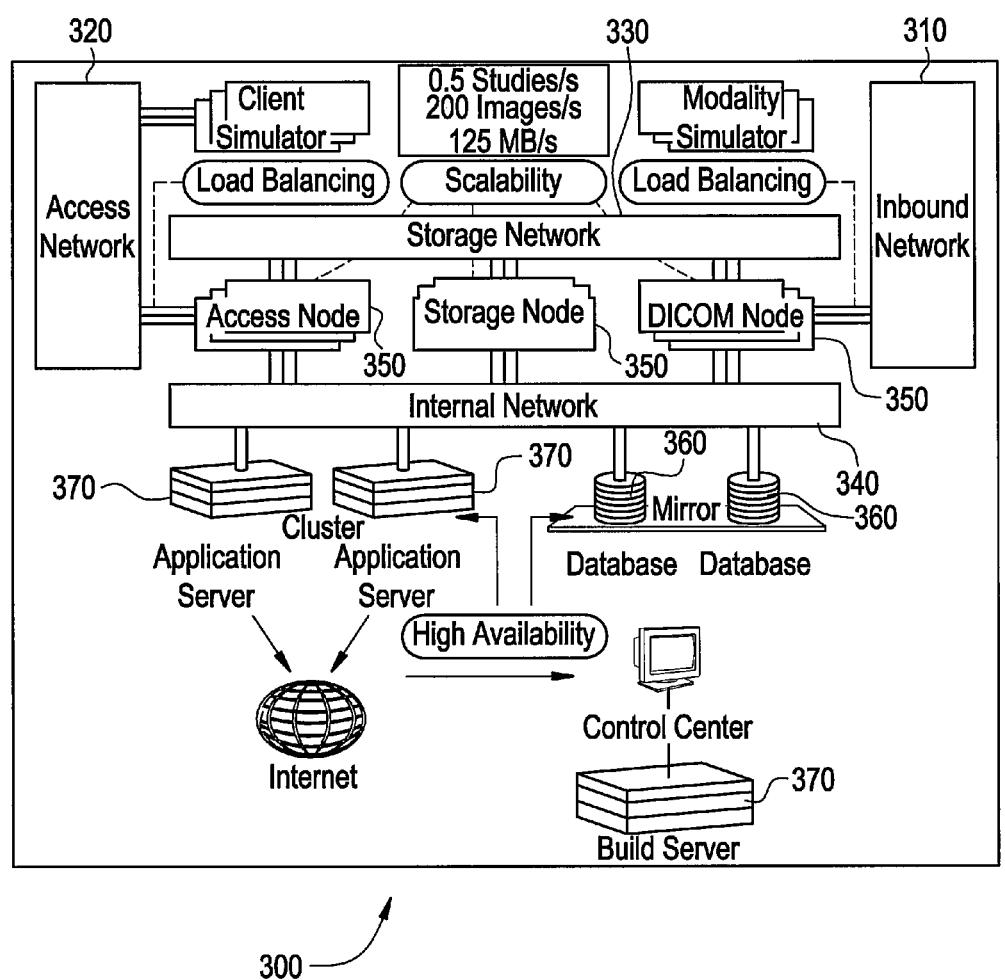
FIG. 3 illustrates a scalable system of sub-assemblies to accommodate various system workflows in accordance with an embodiment of the present invention.
Figure 10:
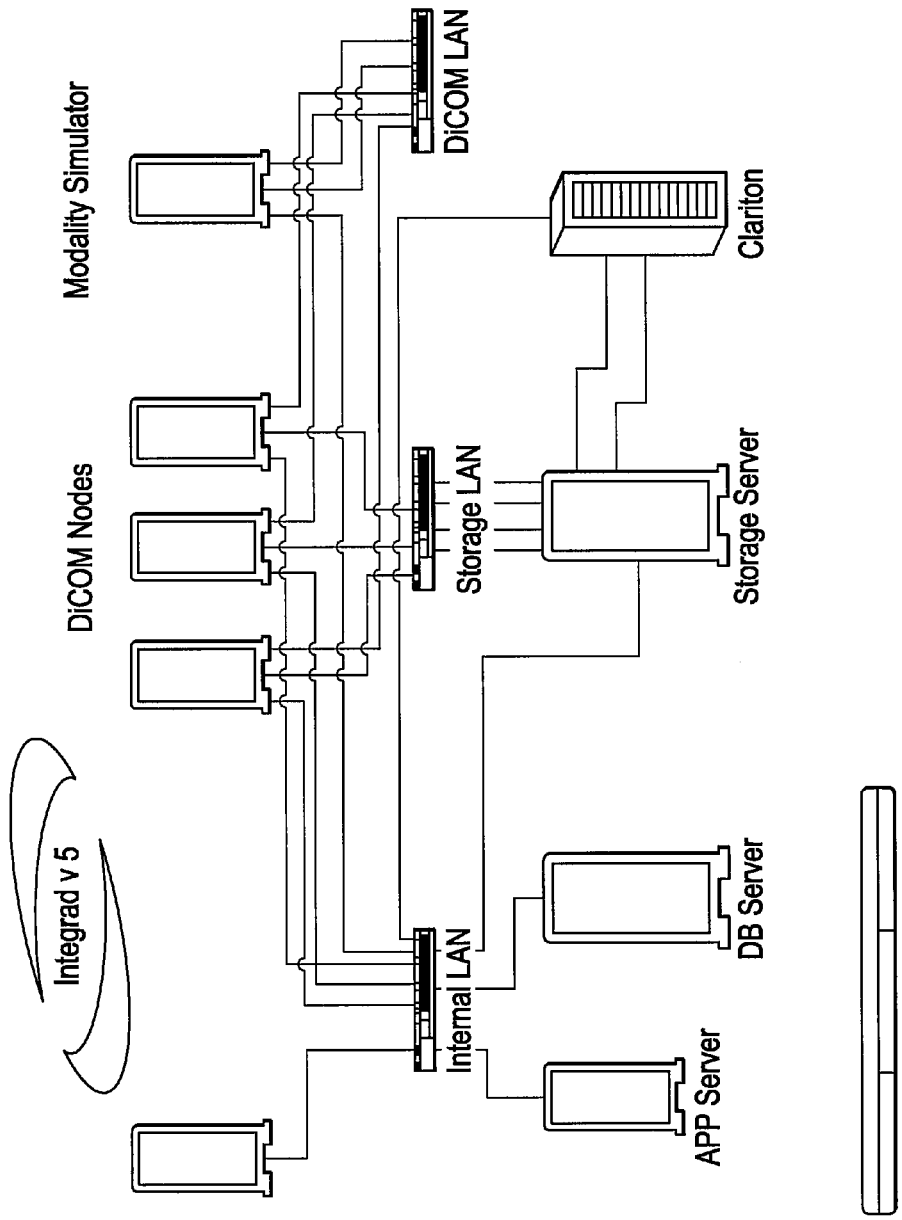
FIG. 10 represents an integrated system in accordance with an embodiment of the present invention.

Certain embodiments provide scalability of system sub-assemblies allowing for independent performance escalation of various system workflows as demonstrated in FIG. 3 representing a performance test bench developed and physically integrated according to certain embodiments of the present invention as represented in FIG. 10. In FIG. 3, the system 300 provides scalability by dividing data, applications, and other services among a plurality of layers and sub-systems. For example, the system 300 includes an inbound network 310, an access network 320, a storage network 300, and an internal network 340 providing information exchange between a plurality of nodes 350, databases 360, servers 370, and the like.

Certain embodiments deliver a clinical product meeting a plurality of requirements including a multi-specialty workflow, a clinical repository, a federation, unlimited scalability (e.g., over five million medical exams annually on hardware typical for 2006), high performance, adaptive workflow, business continuity, perceptive intelligence, system health and business intelligence, and/or multilingual capability, for example.

Certain embodiments help deliver a reliable product meeting business requirements included reduce cost of implementation and support, a solution for upgrade problems, a solution for federated systems, and/or proactive support and monitoring, for example.

Another goal of certain embodiments is to sufficiently improve a development process in part of effective development of wide range of applications, development and maintenance of code for a long period of time (e.g., 7-10 years), and/or fast development with high quality and low cost, for example.

Additional development goals traditionally associated with challenges of software engineering include fast parallel development, high quality by an average developer, multiple distributed workflows and applications, multiple integrations with third party systems, maintainable code despite wide range of features, write applications with less lines of code, reliable technical platform with infrequent changes, and/or automated build, testing and deployment process, for example.

These and goals are achieved through a platform including the following cornerstones and building blocks including a simple architecture, decoupling between technical and business layers, layers providing composable abstractions, keeping development tools to minimum (e.g., using 95% Visual Studio+C#), Domain Specific Extensions (DSE) to C# language for declarative programming, unit testing as intrinsic component of architecture and intrinsic step of the development process, and/or intrinsic automated build/test environment supported on architectural level, for example.

Figure 4:
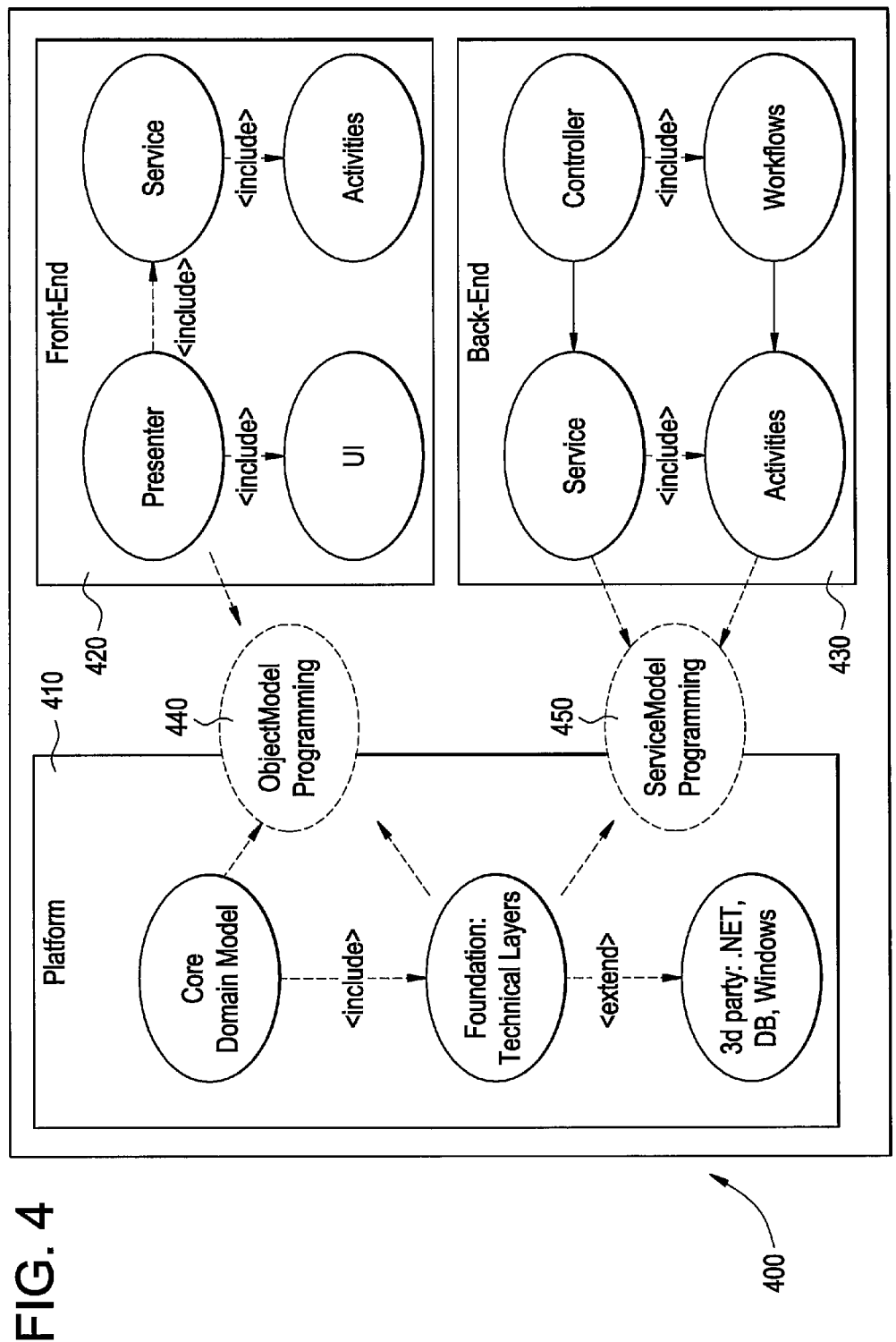
FIG. 4 shows platform architecture in accordance with an embodiment of the present invention.

A simple platform architecture is achieved by: (a) few logical components and programming models, and (b) clear responsibilities and wide applicability of each assembly as demonstrated by FIG. 4. As shown by the system 400 of FIG. 4, functionality may be divided among a platform 410, a front-end 420, and a back-end 430. Components may be divided among a service site, a customer site, and a client computer, for example. Model programming, such as Object Model 440 and Service Model 450 programming, may be used to tie front-end 420, back-end 430, and platform 410 functionality together. As shown in FIG. 4, controller and workflow information, along with service and activity functionality, can be provided by the back-end subsystem 430, which interacts with the models of the particular platform 410 to provide object models to the front-end subsystem 420. The front-end subsystem 420 provides a user interface and presentation functionality for a user.

Certain embodiments provide a programming platform to support building of a novel platform architecture. The programming platform provides separation between two programming models and categories. Certain embodiments separate ObjectModel Programming including (a) Entities, Values, Lenses, Blobs, Queries; (b) Triggers, Indices, Assertions; (c) Transactions; and/or (d) Persistence, for example, and ServiceModel Programming including (a) Manageable servers and services; (b) Distributed and asynchronous activities; (c) Replicated shared objects; and/or (d) Automated change management, for example. Certain embodiments also provide separation between (1) a Domain Model Component category, which includes (a) core business rules and relationships, for example, (2) a Service Component category, which includes (a) Resource scheduler (e.g., defaults are good for most cases); (b) Stateless methods in service; and/or (c) State and application logic kept in service provided activities, for example, and (3) a Server Component Category, which includes (a) Assembly and configuration of services; and/or (b) Presenter and UI Components, for example.

Figure 5:
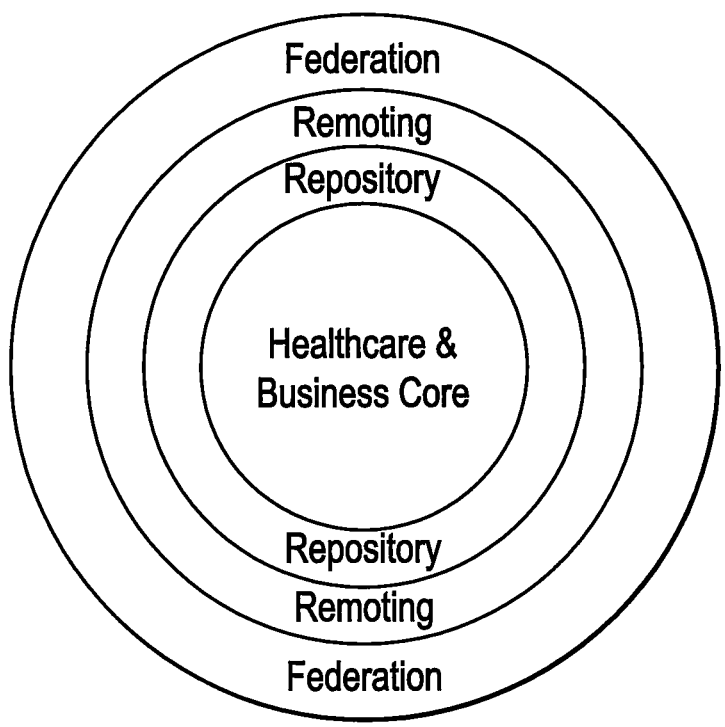
FIG. 5 shows a layered model of a system architecture used as a basis for domain oriented information systems and/or applications in accordance with an embodiment of the present invention.

Certain embodiments provide a novel layered architecture for IT systems developed for a certain business domain such as but not limited to radiology and/or healthcare enterprise and/or other businesses involving distributed information systems (IT) that handle multiple object types of differing natures and lifecycles. Systems serve a variety of users having various subspecialties and working according to various workflows. FIG. 5 shows a layered model of a system architecture used as a basis for domain oriented information systems and/or applications. However, most known layered architectures have one common intrinsic problem related to incorrect dependencies. Namely, business logic depends on everything around it, and, thus, any change in business logic normally involves major modification of the entire system that touches basically all layers of software objects.

Certain embodiments provide a solution to the problem of incorrect dependencies and major modification of the entire system by inverting the system dependencies.

The prior art includes various recipes for inversion, but these methods have all proven to be unsuccessful. In contrast, certain embodiments provide: (a) composable layers; and (b) domain specific language extensions provided by an application domain platform.

Domain Specific Extensions (DSE) provided in certain embodiments allow for many architectural advantages for development and support of multi-specialty applications within the same IT system, each of these advantages supported by a separate inventive element of the overall system. For example, certain embodiments include DSE to make utilization of multiple compositions of layers for different tasks and objects practical in the system. Certain embodiments include DSE to make declarative programming practice in the system. For example, structure (diagrams) is clearly visible in code, and behavior can be understood from the structure. A product diagram may be directly translatable into code. Certain embodiments support compile time validation versus runtime validation.

In certain embodiments, DSE methods provide advantages over Domain Specific Languages (DSL) known in the prior art. For example, DSE allows for a better learning curve for average C# programmer than DSL. DSL usually has pure tool support, while DSE has VS and 3d party extensions. DSL is difficult to maintain, while DSE only slightly extend semantics existing in C# language.

One of the convincing examples of the advantages of DSE engineering is the separation of work between a highly qualified system architect and an average C# programmer. In fact, an architect defines DSE policy through building certain domain specific objects and supports these objects through accommodating a programmed policy to the new requirements arising through a lifecycle of a product. In contrast, a programmer uses an appropriate Domain Specific Object to implement the business logics of any of a multiplicity of workflows and applications supported by the information system. Thus, changing the workflow of the application does not require regression testing of all "system policy" blocks shared by this and other applications. Similarly, changing the policy of the system does not require re-coding each and any application obedient to that policy. This is demonstrated by exception handling implemented through an inventive DSE mechanism as illustrated in part by the pseudocode below:

```
// Architect programs this layer
class ClientPolicy;DefaultExceptionPolicy
{
[ExHandler]
void MyHandler(DicomParserException e, ExceptionContext ctx)
{
throw now NetSupportedObjectFormat(a);
}
}
// Programmer codes:
[ExPolicy(typeof(ClientPolicy)]
class MyClientCode
{
```

-continued

```
[Ex]
void ParseDicomObject( )
{
// calling into DICOM Toolkit leads to
throw new DicomParserException("....");
}
}
```

Thus, certain embodiments provide a novel platform technology for secure handling of objects that have connected simultaneous representations inside and outside a database. Certain embodiments provide a unique solution for unified transactions and secured integrity over objects simultaneously represented by multiple components, some of which are inside the database and others outside the database.

For example, an embodiment provides an implementation of an image repository system.

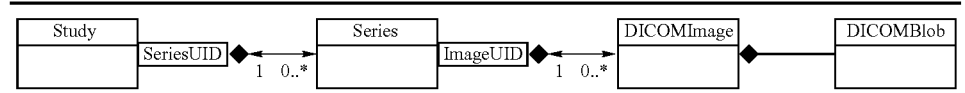

```
[Transactional] class Study
{
[Owned]
public readonly Map<DICOMUID, Series> Series;
bool AddSeries(DICOMUID uid, out Series Result)
{
return Model.NewOrGet(Series, uid, out Result);
}
}
[Transactional] class DICOMImage
{
public DICOMBlob Compressed;
public DICOMBlob Original;
}
class DemoRepository: SqlRepository
{
public readonly Extent<Study> Studies;
public readonly Area OnlineArea;
}
```

Figure 6:
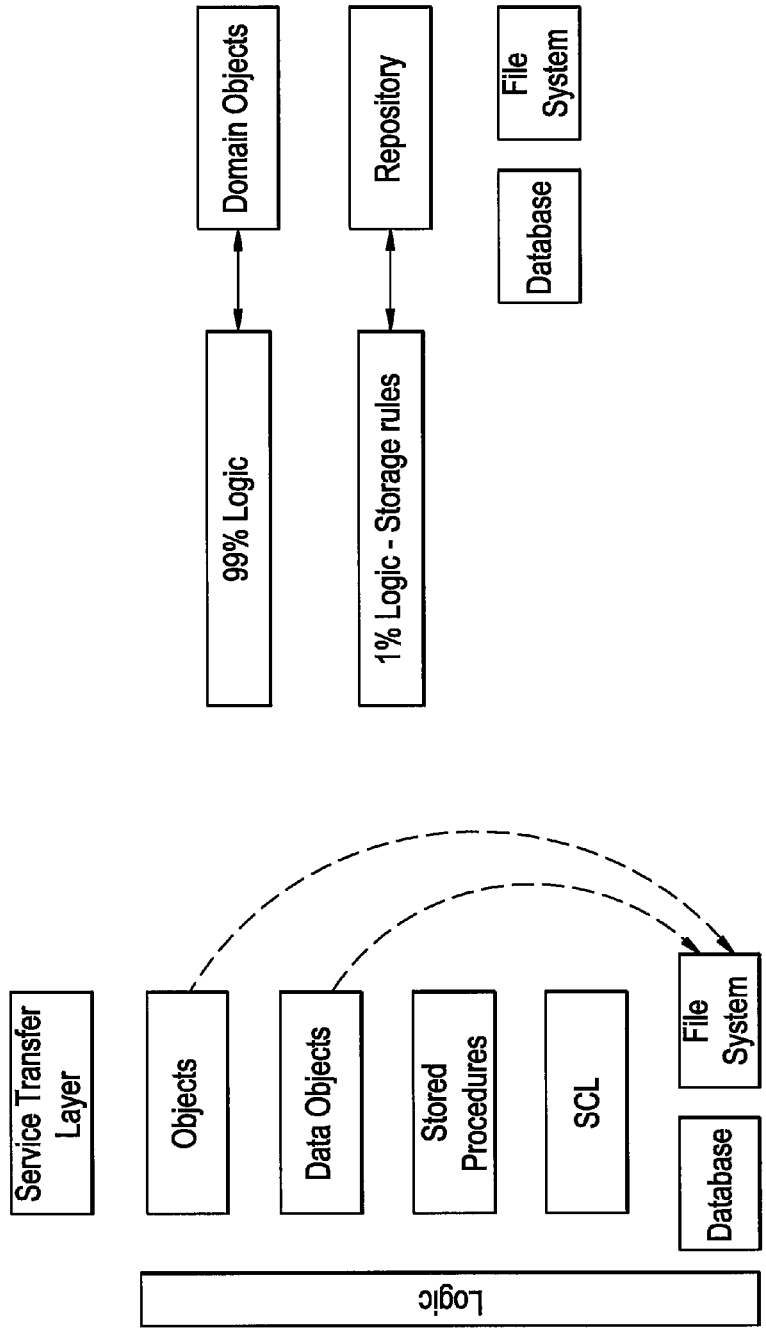
FIG. 6 illustrates a system implementing enterprise-level logic via a smart creation of domain objects in accordance with an embodiment of the present invention.

The system of FIG. 6 facilitates implementing enterprise-level logic via "smart" creation of domain objects. Implementation of specific workflows involves an addition of some application-level logic to basic enterprise-wide rules governing a life-cycle of the domain objects. Storage rule logic allows the objects to interact with a repository, database, file system, etc.

A Platform Provided Domain Model may include, for example, more than 150 implemented Radiology objects covering PACS and RIS, such as Patient, Exam, Visit, SR, DICOM Blob, etc. Thus, the Platform Provided Repository Service may be extensively used by application implemented back-end workflows. For example, Repository Service Activities including but not limited to Transfer and Cache, Replicate, Move, Write, Read, Volume Operation (online/offline/restore), etc., may use Platform Provided Repository Services.

In certain embodiments, multi-specialty information systems are represented by a variety of objects and workflows that are simultaneously represented inside and outside of a database (including but not limited to image records within the database and image data located on the file system and/or external storage, tasks records and task executables currently running on a same server node as the database or even on an external node, etc.). The variety of objects and workflows has introduced problems in traditional systems including but not limited to large amounts of poorly structured read-only data, business logic located in one or multiple places (outside of the database), multithreading programming (outside of the database), reliability and error recovery, etc.

In the above example, the prefix [Transactional] indicates that all handling of the objects defined in that statement should obey the transactional policy. For example, a transaction policy may specify that (1) only one transaction can be applied at a time to any given object, (2) transaction can be rolled back if any unexpected exception happens in the time of transaction over any element of the object in transaction, and/or (3) additional rules and restrictions that, once defined by system architect, are then uniformly applied to all system business objects created using the definition of an appropriate domain object.

Additionally, certain embodiments provide a specific implementation of the transaction mechanism supporting a wide variety of secure transactions being implemented in a Random Access Memory (RAM) and a Central Processing Unit (CPU) of a computer according to a C or C# style coded algorithm, rather than by various native database procedures such as provided by Oracle, Sequel, or other commercial databases. The in-memory transaction handling alleviates the load on the data base and allows for avoiding many data collisions and deadlocks that degrade performance in bulky and sophisticated information systems.

Figure 7:
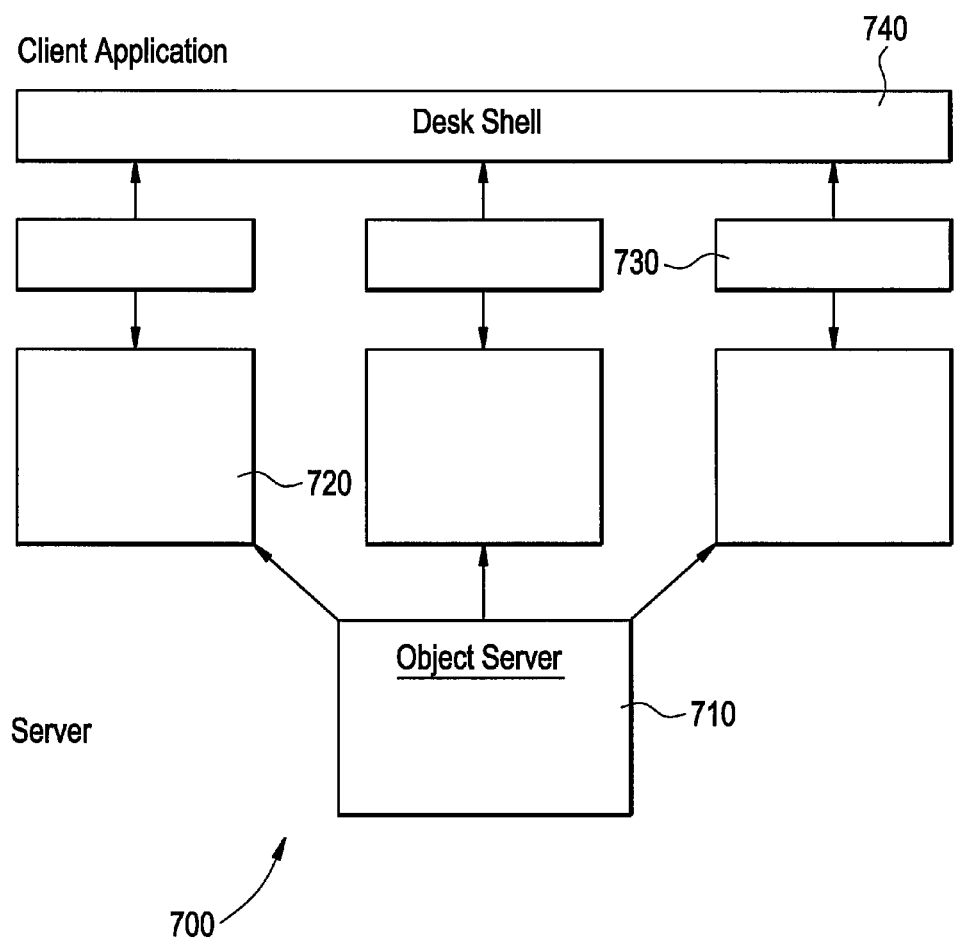
FIG. 7 illustrates an architecture of front-end components, thin and thick clients, and applications running partially on client workstations in accordance with an embodiment of the present invention.

Certain embodiments provide a novel architecture of front-end components including but not limited to a Graphical User Interface (GUI), thin and thick clients, applications running partially on the client workstations, and others. One embodiment of this architecture is presented in FIG. 7. The architecture 700 of FIG. 7 provides the following definite advantages for multi-specialty system development, support and evolution. For parallel development, a system can be divided into independent applications and application modules. Modules designed for one application can be reused in other applications. There is no need to split teams based on physical tiers (e.g., a client team and a server team). An object server 710 can communicate with applications 720 and application modules 730 to provide functionality to a user via a desk shell 740 running on a client workstation. Applications 720 can run partially on a client workstation and partially on a server, for example.

Additionally, certain embodiments provide GUI programming and logic connecting the GUI to object structure and behavior on all tiers of the system. A GUI programming Front-end Module includes 2 assemblies: a core assembly including services and activities and client assembly including presenters and GUI. In addition to this front-end breakdown, a special combination of View and Presenter Objects is provided through an inventive binding mechanism unknown in the prior art.

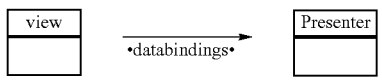

A View object may be implemented based on Microsoft .NET forms technology. A View object may be responsible for screen layout and visual/interactive effects. A View object may provide an easy and gradual migration path to a windows presentation foundation (WPF).

A Presenter object may be implemented based on Microsoft Client Application Block (CAB) and ObjectModel layer technology. A Presenter object may include all application logic. Unit tests may be applied via the Presenter object, for example.

Data binding may be based on Microsoft .NET forms technology. Data binding can help ensure that property of a presenter object corresponds to property of a control object. Data binding includes an add-on to the .NET technology that implements a DSE approach to help ensure compile time validity and re-factoring of objects on a stage of code development and compilation rather than in response to a unit test failure and problem reports from the field.

As a result of this approach, a GUI skin for an application is detached from business rules coding and can be easily changed by inexpensive specialists in reply to field feedback, application modification, and/or regional customization to a new country or language, for example. Application logic and GUI logic can be naturally detached from the GUI controls themselves. Thus, init-testing or application testing do not require additional human action and can be relayed on to an automated testing system. Further, sufficiently small changes of the business logic do not necessarily require simultaneous change of the GUI skins.

With respect to a healthcare information system and particularly a radiologist worklist containing exams assigned to each physician, this approach delivers improved performance in many areas. For example, the system and worklist can support large search/sort results (e.g., 100K entries) without delivering the whole data set to a client. The system allows scrolling through large lists as well as fast display of a first screen and personalized columns, fonts, etc. Certain embodiments provide real time worklist synchronization, on-the-fly filtering, and the like.

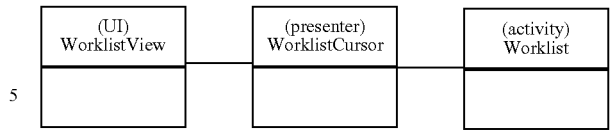

In certain embodiments, Domain Specific Extensions, Data Binding Rules, Transactional Policy and other mechanisms are enforced by a special platform-based policy that creates unit-test cases and a testing infrastructure as an integral step of code development and code compilation. As a result, upon each new build of modified code, unit test code is automatically created and executed, and all results of the unit tests are immediately summarized and delivered for analysis.

In certain embodiments, a special Remoting Layer may be implemented on top of a service layer and may constitute an intrinsic part of the platform. The Remoting Layer may be based, for example, on Microsoft Windows Communication Foundation (WCF) and provides: protocol independence, security, integration between different internal and external objects and applications, etc. Since the Remoting Layer is part of the platform, some selected objects, including but not limited to data objects, cached objects, workflows, computational engines, and others, can be instructionally allocated and adaptively moved between different hardware units across an entire Information System.

In certain embodiments, adjacent to the Remoting Layer is another inventive paradigm and appropriate mechanism of Adaptive Workflow as implemented on a level of the system platform and presuming the following. Adaptive Workflow assumes that workflow is a unit of system configuration. Additionally, Adaptive Workflow uses C resource allocation: workflow is defined in logical terms, and resource allocation is derived from logical flow. Resource allocation is transformed into an execution plan. Further, the system is aware of pending workflows and is capable of increased or optimal management of resources.

Examples of implementation of this paradigm include server side processing vs. client processing. Additional examples include load balancing between different hardware engines executing essentially alike tasks. Further examples include prioritization for insertion and transfer of images, images distribution and caching.

Figure 8:
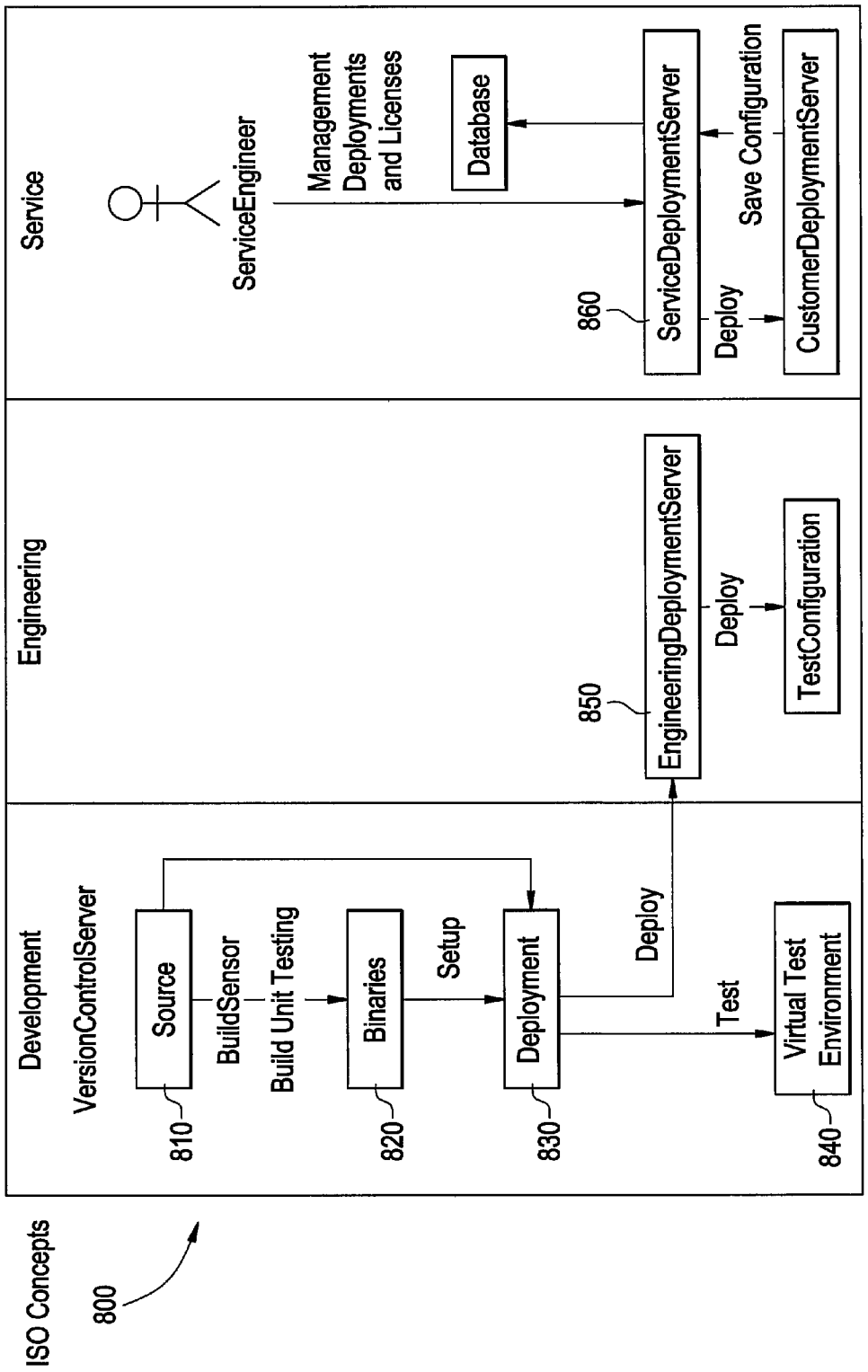
FIG. 8 illustrates a product deployment concept in accordance with an embodiment of the present invention.

In certain embodiments, a Novel Deployment Concept includes steps of product release and deployment that are programmed and configured in the course of the product development using unique features and services delivered by the platform designed in accordance with certain embodiments of the present invention. Basics of this Deployment Concept are presented in FIG. 8 and constitute successive steps which are completely programmed and scheduled for implementation and execution in the course of development. These steps 800 include but are not limited to labeling of sources automatically picked for building of a product version 810, building the new version 820, and building of deployment for all setup routines 830. The steps also include building of a unit testing system and building of a test and execution environment 840. The steps further include deployment of the newly built components on the test environment for engineering department and execution of the tests 850. Upon successful testing, relevant objects are automatically ported to the relevant service centers 860.

Upon command from the service centers, relevant components are deployed to customer sites in the field. Additionally, old system components and configuration are backspun, and a site's software version and/or configuration are upgraded. Further, the new environment is tested. An upgrade or rolling back and delivering of an error report to service center may be approved.

Figure 9:
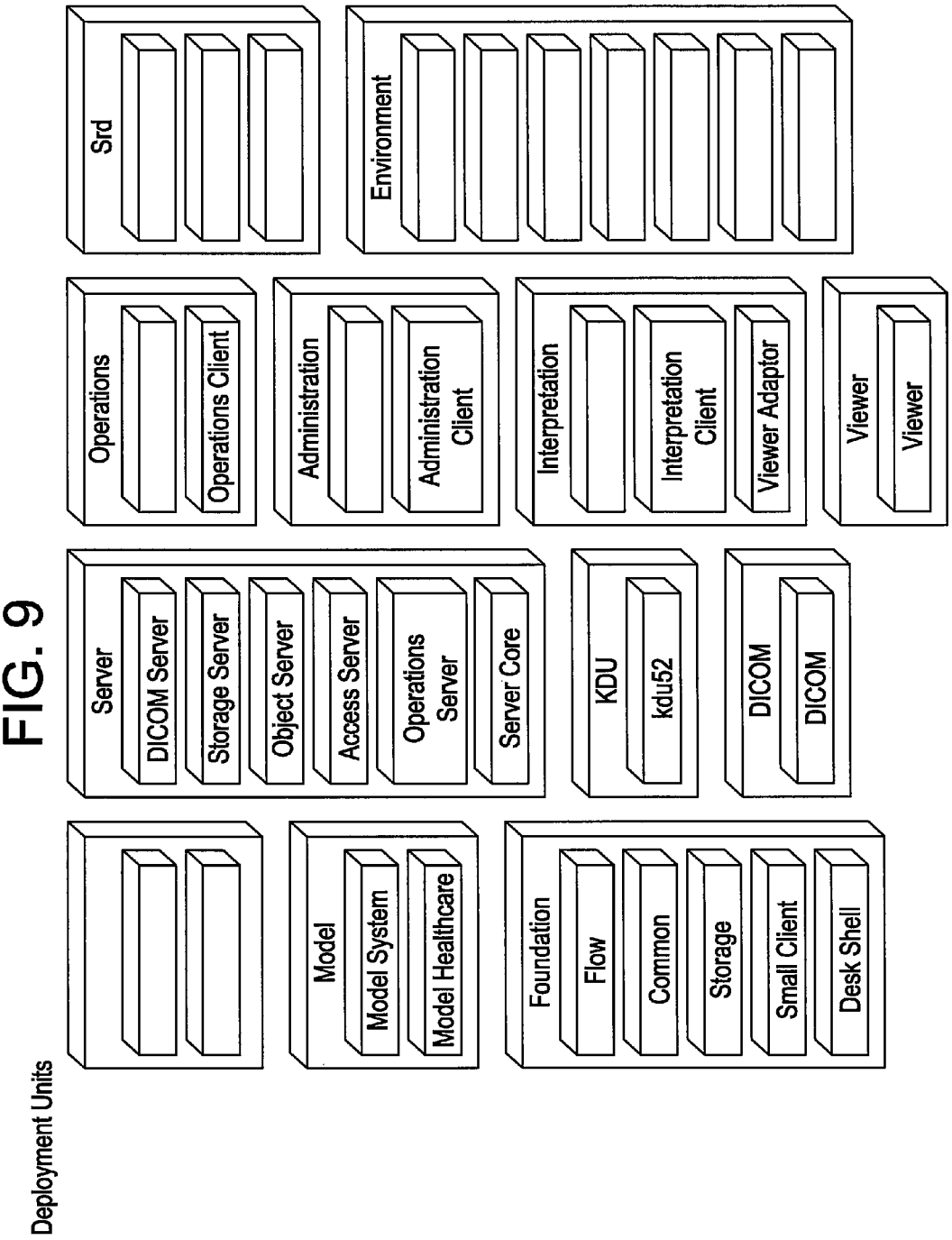
FIG. 9 depicts a system of objects and services in accordance with an embodiment of the present invention.

This chain of actions is supported by a sophisticated system of objects and services which are schematically presented in FIG. 9 in accordance with an embodiment of the present invention.

In certain embodiments, the system platform delivers specific tools and services that are used in system monitoring and system intelligence components of a final product. Certain embodiments of implemented assemblies are presented in FIG. 11 and FIG. 12. According to certain embodiments, such designed system monitoring and system intelligence modules are naturally created in a course of development by various components, tools, and paradigms intrinsic to the platform and including but not limited to DSE, Remoting, Adaptive Workflows, and others. According to an embodiment, the same tools and subassemblies that deliver system monitoring and system intelligence are re-used upon system development in unit- and performance-testing deficiency analysis and other activities including Quality Assurance, System Validation, Performance Watch, Regression Testing and other release efforts.

Figure 11:
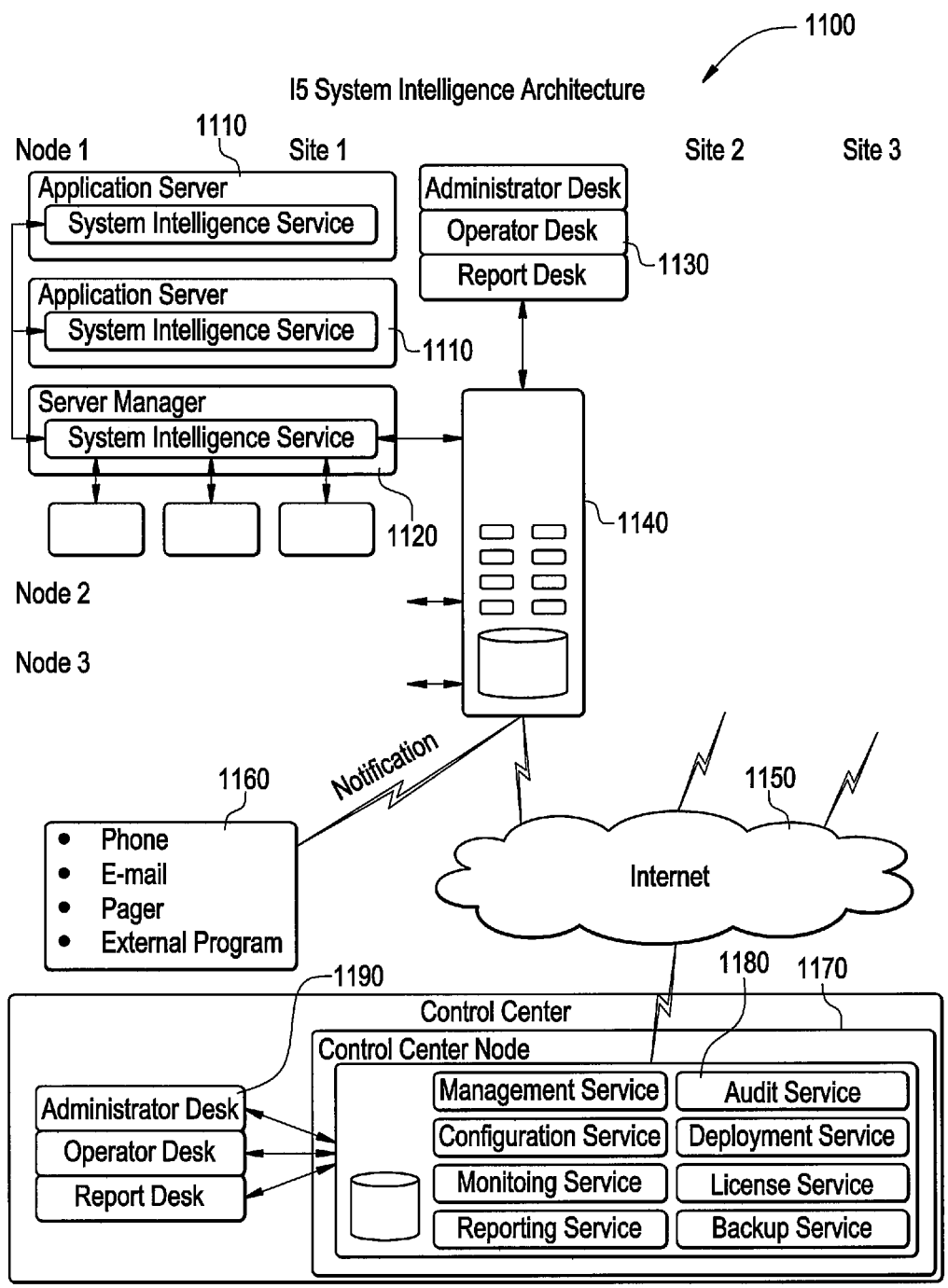
FIG. 11 illustrates an implemented system assembly in accordance with an embodiment of the present invention.

As illustrated in FIG. 11, a system intelligence architecture 1100 includes one or more application servers 1110, a server manager 1120, one or more desk modules 1130, a site node 1140, a network 1150, a notification module 1160, and a control center 1170. The control center 1170 includes a control center node 1180 and one or more desk modules 1190. The application server(s) 1110 include a system intelligence service and are coordinated by the server manager 1120 to communicate with a site node 1140. The site node 1140 also communicates with one or more desk modules 1130 including an administer desk, an operator desk, and/or a report desk, for example. The node 1140 may generate and/or receive a notification 1160 such as a phone, email, pager, and/or external program notification, for example. The node 1140 may communicate via the network 1150, such as the Internet or a private network, to the control center 1170. The control center node 1180 of the control center 1170 also communicates with one or more desk modules 1190, such as an administrator desk, an operator desk, and/or a report desk, for example. The control center node 1180 includes a database or other storage, as well as one or more services. Services can include a management service, a configuration service, a monitoring service, a reporting service, an audit service, a deployment service, a license service, and/or a backup service, for example.

Figure 12:
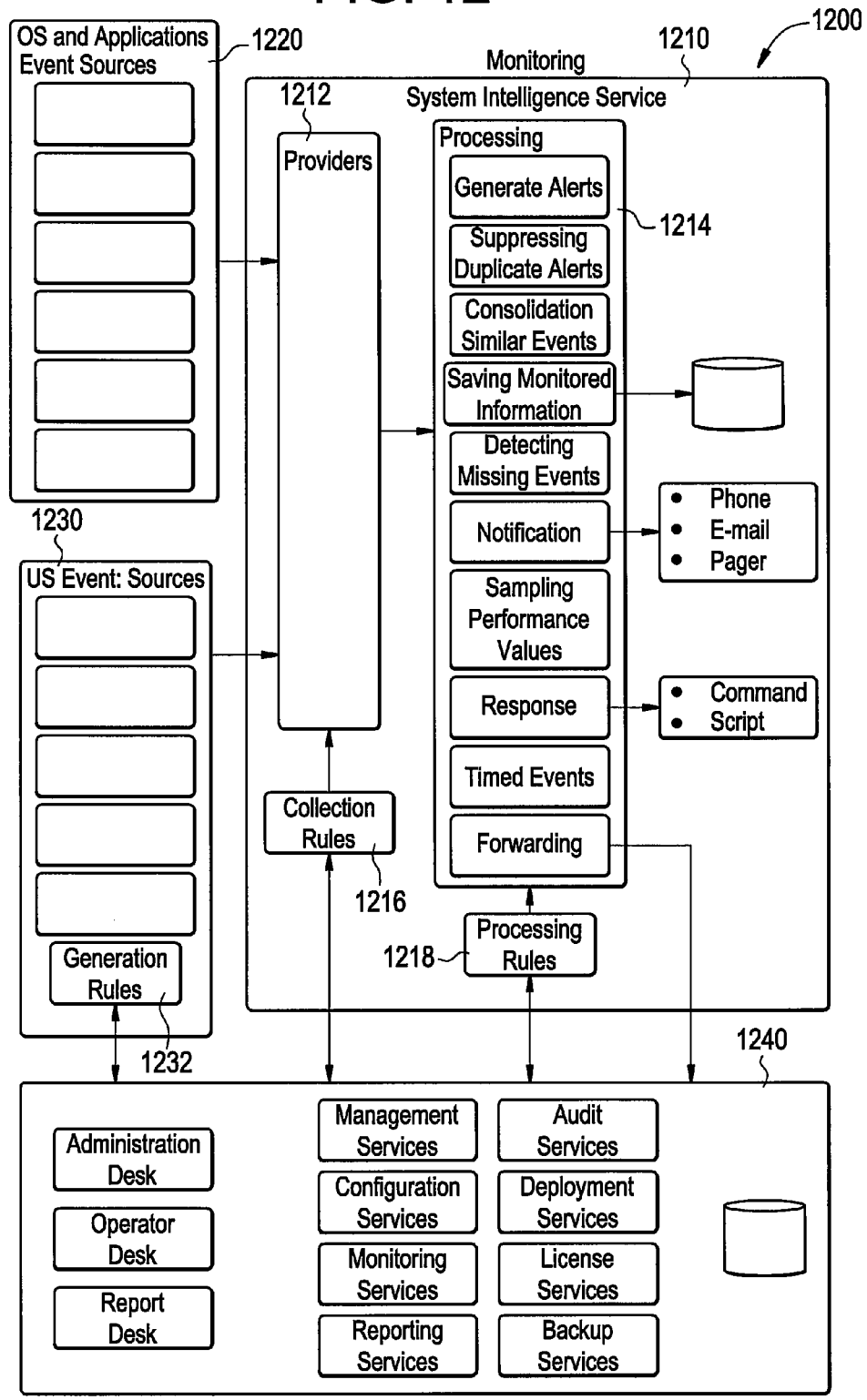
FIG. 12 illustrates an implemented system assembly in accordance with an embodiment of the present invention.

As illustrated in FIG. 12, a monitoring system 1200 includes a system intelligence service 1210, one or more event sources 1220, 1230, and a control center 1240. Event sources, such as operating system and application event sources 1220 and/or other event sources 1230, provide information to the system intelligence service 1210. Even sources may include rules 1232 relating to generation of events, for example. The control center 1240 includes local storage, desk modules (such as administrator, operator, and/or report desk modules), services (such as management, configuration, monitoring, reporting, audit, deployment, license, and/or backup services), and the like. The components of the control center 1240 provide information to and/or receive information from components of the system intelligence service 1210. The system intelligence service 1210 includes a providers module 1212, a processing module 1214, rules (such as collection rules 1216 and processing rules 1218), local storage, notification information, command/script generation, etc. The providers module 1212 receives event information from the event sources 1220, 1230 based on collection rules 1216, and provides event information to the processing module 1214. The processing module 1214 processes the event information based on the processing rules 1218 and provides one or more results from the event processing. For example, the processing module 1214 may generate alerts, suppress duplicate alerts, consolidate similar events, save monitored information in local and/or remote storage, detect missing events, provide notification (e.g., phone, e-mail, and/or pager notification), sample performance values, generate a response (such as a command and/or script), generate timed events, and/or forward events, etc. Rules, such as generation rules 1232, collection rules 1216, and/or processing rules 1218 can communicate with the control center 1240 for updates, changes, etc. The processing module 1214 can forward event information to the control center 1240 as well, for example.

Thus, certain embodiments provide a technical effect of a sub-divided, modular and scalable information system. Certain embodiments distribute data and processing among a server, a customer site, and a client computer. Certain embodiments provide composable layers and domain specific extensions to enable functionality at a user workstation. Certain embodiments, provide streamlined development and system monitoring capability. Certain embodiments separate Domain Model components, Service components, and Server components, as well as Object Model and Service Model programming, to provide a flexible, decoupled system to users. Certain embodiments provide a healthcare information system, such as a PACS, including a front-end GUI, a platform hosting Domain Specific Extensions, and a back-end providing services, applications, workflows, and the like.

It should be understood by any experienced in the art that the inventive elements, inventive paradigms and inventive methods are represented by certain exemplary embodiments only. However, the actual scope of the invention and its inventive elements extends far beyond selected embodiments and should be considered separately in the context of wide arena of the development, engineering, vending, service and support of the wide variety of information and computerized systems with special accent to sophisticated systems of high load and/or high throughput and/or high performance and/or distributed and/or federated and/or multi-specialty nature.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain embodiments of the present invention may omit one or more of the method steps and/or perform the steps in a different order than the order listed. For example, some steps may not be performed in certain embodiments of the present invention. As a further example, certain steps may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A distributed healthcare information system, said distributed information system comprising:
    a back-end subsystem configured to provide content including radiology services, applications, and workflows for healthcare execution, said content configured for general application to a plurality of healthcare domains and said content divided into a plurality of composable layers to be customized according to a selected healthcare domain, the back-end subsystem configured to provide said content including controller and workflow information along with service and activity functions;
    a platform subsystem including a plurality of platform provided domain models, said platform subsystem configured to provide domain specific extensions to customize said content of said back-end subsystem for particular healthcare domains, said domain specific extensions to compose layers of said content based on said selected healthcare domain to support a radiology workflow associated with said selected healthcare domain, said platform subsystem in communication with said back-end subsystem to access said content including said workflow information from said back-end subsystem, said back-end subsystem to provide said service and activity functions to interact with one or more of the platform provided domain models provided by the platform subsystem based on said selected healthcare domain to generate object models, said object models generated for the selected healthcare domain to include radiology object models to implement a radiology system and services for a requesting user; and
    a front-end subsystem configured to provide a customized graphical user interface for a user to access functionality and information based on said content as customized by said domain specific extensions, said front-end subsystem in communication with said platform subsystem to access said content including said object models based on said selected healthcare domain to support said graphical user interface and associated presentation functionality to implement the radiology system and services for user interaction,
    wherein each of the front-end subsystem, back-end subsystem, and platform subsystem comprise a processor and a memory, and wherein the subsystems are configured to provide an adaptive workflow to develop available resource allocation based on pending workflows, the adaptive workflow to be divided according to operations and data workflows such that the workflows are able to be escalated separately, the resource allocation to be transformed into an execution plan to be implemented by the system.

2. The system of claim 1, wherein said front-end subsystem is located at a client computer, said platform subsystem is located at a customer site, and said back-end subsystem is located at a service site.

3. The system of claim 1, further comprising service model programming to facilitate interaction between said back-end subsystem and said platform subsystem.

4. The system of claim 1, further comprising object model programming to facilitate interaction between said platform subsystem and said front-end subsystem.

5. The system of claim 1, wherein said back-end subsystem and said platform subsystem decouple technical layers and business layers for said content.

6. The system of claim 1, wherein said platform subsystem comprises data binding rules and transactional policy in addition to said domain specific extensions.

7. The system of claim 1, further comprising a testing infrastructure to facilitate code development and testing for said distributed healthcare information system.

8. The system of claim 1, further comprising a remoting layer providing protocol independence, integration, and security.

9. A method for distribution of healthcare information and functionality, said method comprising:
retrieving, from a back-end subsystem, generalized content based on a request from a user interface front-end, said content including radiology services, applications, and workflows for healthcare execution, said content configured to be generally applicable to a plurality of healthcare domains and said content divided into a plurality of composable layers to be customized according to a selected healthcare domain, the back-end subsystem configured to provide said content including controller and workflow information along with service and activity functions;
associating, via a platform subsystem including a plurality of platform provided domain models, one or more domain specific extensions with said generalized content to customize said content for a particular healthcare domain, said domain specific extensions to compose layers of said content based on said selected healthcare domain to support a radiology workflow associated with said selected healthcare domain, said platform subsystem in communication with said back-end subsystem to access said content including said workflow information from said back-end subsystem, said back-end subsystem to provide said service and activity functions to interact with one or more of the platform provided domain models provided by the platform subsystem based on said selected healthcare domain to generate object models, said object models generated for the selected healthcare domain to include radiology object models to implement a radiology system and services for a requesting user;
providing said content with said one or more domain specific extensions to a user via said user interface front-end, said user interface front-end in communication with said platform subsystem to access said content including said object models based on said selected healthcare domain to support said user interface front-end and associated presentation functionality to implement the radiology system and services for user interaction; and
facilitating an adaptive workflow to develop available resource allocation based on pending workflows, the adaptive workflow to be divided according to operations and data workflows such that the workflows are able to be escalated separately, the resource allocation to be transformed into an execution plan to be implemented by the system.

10. The method of claim 9, wherein said user interface front-end is located at a client computer, said one or more domain specific extensions are located on a platform subsystem at a customer site, and said generalized content are located on a back-end subsystem at a service site.

11. The method of claim 9, wherein said associating further comprises utilizing service model programming to associate said one or more domain specific extensions with said generalized content to customize said content for a particular domain.

12. The method of claim 9, wherein said providing further comprises utilizing object model programming to provide said content with said one or more domain specific extensions to a user via said user interface front-end.

13. The method of claim 9, wherein said associating further comprises utilizing data binding rules and transactional policy in addition to said domain specific extensions to associate said one or more domain specific extensions with said generalized content to customize said content for a particular domain.

14. The method of claim 9, further comprising:
labeling of sources that have been automatically selected for building of a product version based on the plurality of composable layers;
building said product version;
building of a deployment process for setup routines for said product version;
building of a test execution environment;
deploying components of said product version in said test environment based on said deployment process; and
automatically porting components of said product version to relevant service centers upon successful testing via said test environment.

15. A distributed information system utilizing domain model components, service components, and server components to provide information and functionality to a user, said distributed information system comprising:
a back-end subsystem configured to provide content including radiology services, applications, and workflows for healthcare execution, said content configured for general application to a plurality of healthcare domains and said content divided into a plurality of composable layers to be customized according to a selected healthcare domain, the back-end subsystem configured to provide said content including controller and workflow information along with service and activity functions;
a platform subsystem including a plurality of platform provided domain models, said platform subsystem configured to provide domain specific extensions to customize said content of said back-end subsystem for particular healthcare domains, said domain specific extensions to compose layers of said content based on said selected healthcare domain to support a radiology workflow associated with said selected healthcare domain, said platform subsystem in communication with said back-end subsystem to access said content including said workflow information from said back-end subsystem, said back-end subsystem to provide said service and activity functions to interact with one or more of the platform provided domain models provided by the platform subsystem based on said selected healthcare domain to generate object models, said object models generated for the selected healthcare domain to include radiology object models to implement a radiology system and services for a requesting user; and
a front-end subsystem configured to provide a customized graphical user interface for a user to access functionality and information based on said content as customized by said domain specific extensions, said front-end subsystem in communication with said platform subsystem to access said content including said object models based on said selected healthcare domain to support said graphical user interface and associated presentation functionality to implement the radiology system and services for user interaction, wherein each of the front-end subsystem, back-end subsystem, and platform subsystem comprise a processor and a memory, and wherein the subsystems are configured to provide an adaptive workflow to develop available resource allocation based on pending workflows, the adaptive workflow to be divided according to operations and data workflows such that the workflows are able to be escalated separately, the resource allocation to be transformed into an execution plan to be implemented by the system.

16. The system of claim 15, further comprising service model programming to facilitate interaction between said back-end subsystem and said platform subsystem and object model programming to facilitate interaction between said platform subsystem and said front-end subsystem.

17. The system of claim 15, wherein said plurality of layers comprise decoupled technical layers and business layers for said content which may be coupled for a particular domain using said domain specific extensions.

18. The system of claim 15, wherein said platform subsystem comprises data binding rules and transactional policy in addition to said domain specific extensions.

19. The system of claim 15, wherein the radiology system comprises at least one of a picture archiving and communication system (PACS) and a radiology information system (RIS).

20. The system of claim 1, wherein the radiology system comprises at least one of a picture archiving and communication system (PACS) and a radiology information system (RIS).

* * * * *